United States Patent
Tatsuduki

(10) Patent No.: US 6,384,896 B1
(45) Date of Patent: *May 7, 2002

(54) MICROFILM SEARCH DEVICE

(75) Inventor: Yoshikazu Tatsuduki, Kanagawa (JP)

(73) Assignee: Unisia Jecs Corporation, Kanagawa (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/165,993

(22) Filed: Oct. 2, 1998

(30) Foreign Application Priority Data

| Oct. 2, 1997 | (JP) | ................................ 9-284313 |
| Nov. 13, 1997 | (JP) | ................................ 9-327228 |

(51) Int. Cl.[7] ............... G03B 27/52; G03B 23/12; H01J 3/14; G01J 1/04
(52) U.S. Cl. ............... 355/41; 353/25; 353/26 A; 250/216; 250/227.11
(58) Field of Search ............... 355/41, 42; D26/27; 385/115, 117; 250/227.11, 227.2, 227.24, 227.26, 559.36, 341.1, 570, 559.02, 559.44, 216; 353/26 A, 25, 26 R, 27 R

(56) References Cited

U.S. PATENT DOCUMENTS

| 3,435,243 A | * | 3/1969 | Webb ................... 250/559.36 |
| 3,629,593 A | * | 12/1971 | Van Brimer ............ 250/570 |
| 4,559,451 A | * | 12/1985 | Curl ..................... 250/559.36 |
| 4,805,991 A | * | 2/1989 | Arai et al. ............. 350/255 |
| 5,006,719 A | * | 4/1991 | Blaser .................. 250/559.36 |
| 5,354,994 A | * | 10/1994 | Hicks .................. 250/559.36 |
| 5,369,721 A | * | 11/1994 | Conti ................... 385/115 |
| 5,389,789 A | * | 2/1995 | Nguyen ................ 250/341.1 |
| 5,585,615 A | * | 12/1996 | Iwanami et al. ........ 235/472 |
| 5,625,468 A | * | 4/1997 | Oosaka ................. 358/487 |
| 5,717,806 A | * | 2/1998 | Pileski et al. ........... 385/117 |
| 5,991,004 A | * | 11/1999 | Wallace et al. ......... 355/53 |

* cited by examiner

Primary Examiner—Russell Adams
Assistant Examiner—Rodney Fuller
(74) Attorney, Agent, or Firm—Sughrue Mion, PLLC

(57) ABSTRACT

A microfilm search device for distinguishing presence of frames from a change in quantity of transmitted light between the opposed optical fiber end faces between which a microfilm is placed. A pair of opposed blocks for holding optical fibers are arranged across the microfilm in a width direction with placing the microfilm therebetween. Light is guided into the optical fibers held by one block from a light source, passes through the microfilm, and enters the optical fibers held by other block. A quantity of entered light is detected by photosensor and an output thereof is binarized. Based on binarized signals, the presence of frames is determined. End portions of optical fibers on the side of the light source are bunched, and a bunched portion is detachably and non-rotatably held relative to one lamp. Frame detection condition due to light quantity can be uniform and maintained easy after disassembly, inspection, maintenance of the device. The each block comprises a metal plate opposing to the film surface and a resin integrally molded on the backside. A surface of the metal plate is polished. The damages of film and/or the end faces of the optical fibers during high-speed running of the film are prevented.

8 Claims, 14 Drawing Sheets

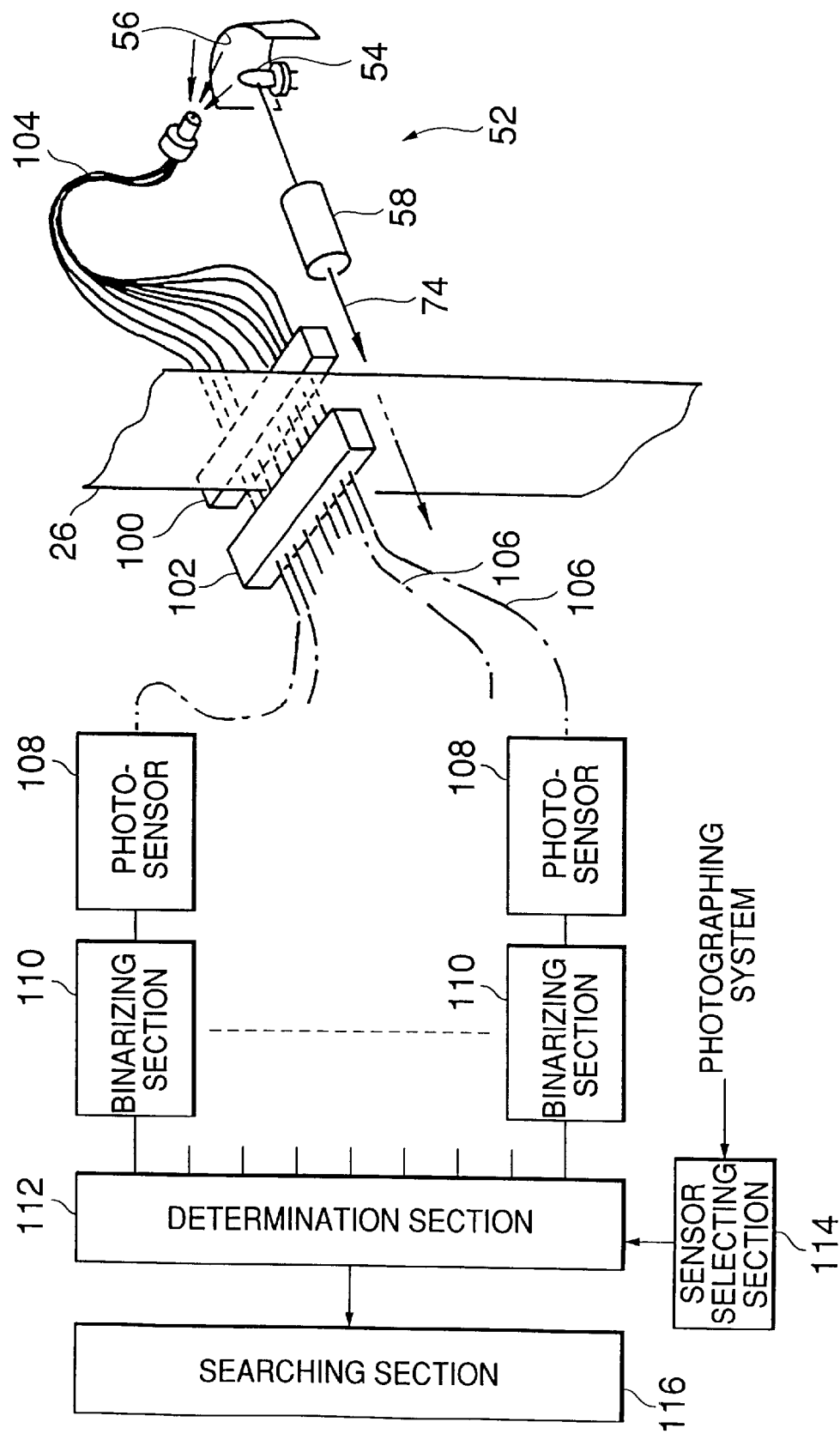

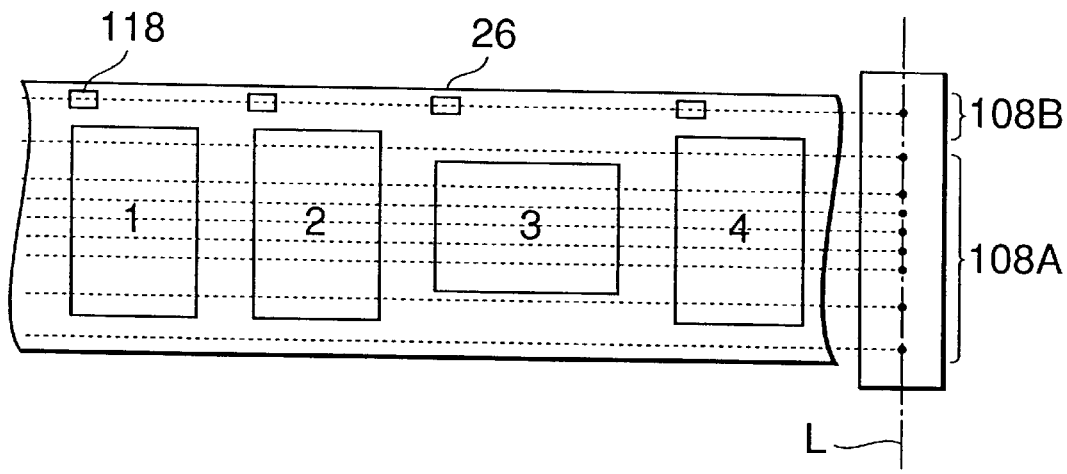
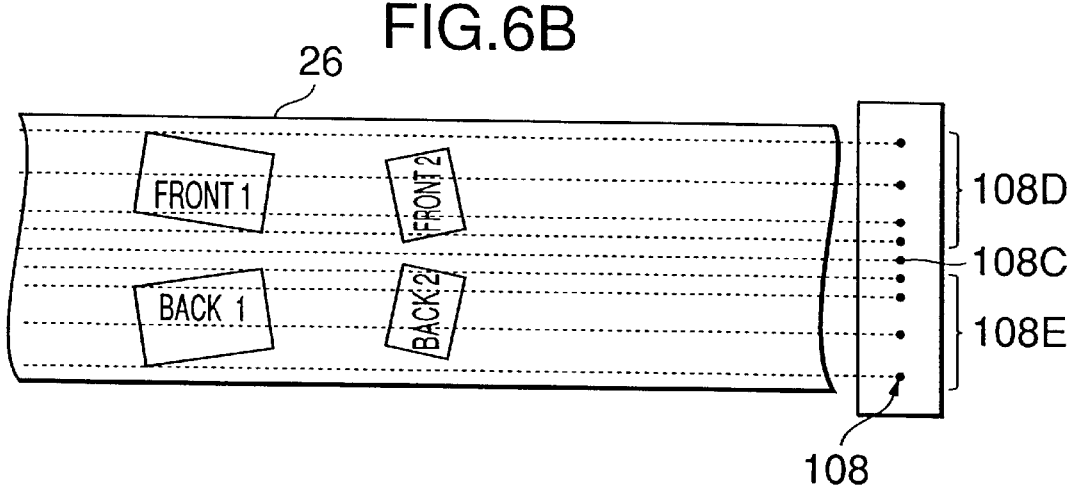
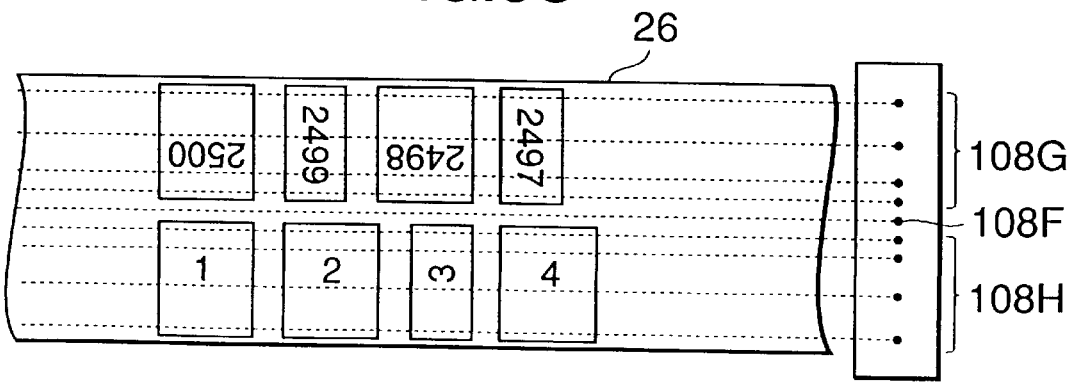

MICROFILM SEARCH DEVICE

BACKGROUND OF THE INVENTION

1. Field of the Invention

The present invention relates to a microfilm search method and device which searches a desired frame by determining the presence of frames from a density change in microfilm running direction.

2. Description of the Related Art

In a known microfilm search method, search marks (blips) are photographed or recorded besides the frames on microfilm and used as reference marks. The blips of microfilm during running are read and counted, and the blip count is used to identify frame addresses when a specific frame is sought.

On the other hand, there is proposed a search method in which, instead of using the blips, the presence of frames is directly detected, and a desired frame is searched for from a sequence of detected frames. Specifically, a density sensor is disposed within the travel width of the frame, so that the presence of frames is determined from a change in film density detected by the density sensor.

In a case where the presence of frames is detected, end faces of a pair of optical fibers between which a film is placed are opposed to each other. Light incident upon one optical fiber is guided to the film, light transmitted through the film is received by the other optical fiber, and the quantity of received light is detected by a photosensor.

In this case, a plurality of pairs of optical fibers for detecting film densities are disposed in different positions along a film width direction, so that the presence of frames is determined using results detected in the different positions. For example, if frame positions along the film width direction are changed by a change in film photographing system, optical fibers for use may be changed. Moreover, by determining the presence of frames using the film densities detected in a plurality of positions within the frame travel width, determination accuracy can be enhanced.

In a case where the presence of frames is determined in a plurality of positions in the film width direction as aforementioned, frame detection conditions of a plurality of pairs of optical fibers need to be uniform. The frame detection conditions are changed by changes, for example, in quantity of light guided to the plurality of pairs of optical fibers from a light source, attenuation characteristics of the optical fibers, characteristics of photosensor, a threshold value for binarizing an output of the photosensor, and the like. Therefore, these conditions need to be maintained as constant as possible.

If the quantity of light guided to each optical fiber from the light source is not constant, the quantity of light guided into the film becomes non-uniform. Moreover, if a light axis of the each optical fiber for receiving light via the film does not align with a light axis of the corresponding opposed optical fiber for guiding light to the film, the quantity of light reached to the photosensor from the light receiving optical fiber becomes non-uniform. When the quantity of light reaching the photosensor is finally non-uniform, the frame detection accuracy is deteriorated.

As aforementioned, the quantity of light guided to each optical fiber from the light source is preferably constant. However, if each light-guiding optical fiber is separately provided with an independent lamp, it is difficult to keep uniform the quantities of light from all the lamps, and conditions become non-uniform even at the time of lamp replacement. Moreover, the entire device is enlarged. Furthermore, it is proposed that light be radiated to the end face of each optical fiber on the side of the light source from one common lamp. In this case, however, if the optical fibers are once separated from the lamp at the time of inspection or maintenance of the device, the relative positions of the optical fibers will be changed when reassembled. A resultant problem is that the quantity of light incident upon each pair of optical fibers changes, the frame detection conditions also change, and the frame detection accuracy is deteriorated.

On the other hand, in order to equalize the frame detection conditions, the light axes of the end faces of the opposite optical fibers between which the film is placed need to be positioned with high precision.

However, the optical fibers are remarkably fine. For example, the inventor of the present application has studied that, to detect frames of a 16 mm wide microfilm, the film density is detected for each film feeding amount of 0.1 mm. In this case, the diameter of the optical fiber needs to be about 0.5 mm. Therefore, it is requested that the positioning or alignment of the light axes of optical fibers can be performed with high precision and that no mis-alignment is generated in the light axes even after long-time use.

To solve the problem, it is proposed that a pair of optical fiber holding blocks arranged across the film in a width direction are opposed to each other between which the film is placed, so that the optical fibers are held by the blocks. Such construction raises other problems. Specifically, since the film runs through a gap between the blocks at a high speed, the film may be damaged at the time of the high-speed running. Moreover, the end faces of the optical fibers are exposed to the opposite surfaces of the blocks. If the end faces of the optical fibers protrude from the surface of the block, the film running at a high speed directly abuts on the end faces of the optical fibers, and the end faces of the optical fibers are damaged or roughed to lower the light incidence or emission efficiency. If the damaging of the film or the irregular roughing of the optical fiber end faces make non-uniform the light incidence/emission efficiency, the frame detection conditions will be affected, resulting in that the frame detection accuracy further lowers. In an addition, when the film running at a high speed contacts with or rubs surfaces of the blocks, static electricity is generated, and the film is electrically charged to generate electrostatic noises. This also adversely affects the frame detection accuracy.

SUMMARY OF THE INVENTION

The present invention has been accomplished in consideration of the circumstances described above, and an object thereof is to provide a microfilm search device in which end faces of a pair of optical fibers are opposed to each other with a film placed therebetween, light incident upon one fiber is guided to the film, light transmitted through the film is received by the other optical fiber, and the presence of frames is detected from a film density change obtained by detecting the quantity of received light with a photosensor, so that the frame detection accuracy can be enhanced.

Another object of the invention is to provide a microfilm search device in which the compactimization of the device is realized, and the quantity of light guided to a plurality of optical fibers is prevented from changing at the time of device disassembly, inspection, maintenance, or the like, so that the frame detection accuracy can be enhanced.

Further object of the invention is to provide a microfilm search device in which a film can run between blocks for holding optical fibers at high speed while preventing damages both of the film and the blocks due to any abut or contact with each other, and in which an electrification of the film is prevented to avoid the generation of electrostatic noises, so that the frame detection accuracy can be prevented from being deteriorated with time.

To attain these and other objects, the present invention provides a microfilm search device for distinguishing presence of frames from a density change in a running direction of a microfilm and searching for a desired frame from the microfilm, comprising:

a first block arranged across the microfilm in a width direction;

a second block arranged across the microfilm in the width direction, end faces of the first and second blocks being opposed to each other with placing the microfilm therebetween;

first optical fibers whose end faces passed through and held by the first block;

second optical fibers whose end faces passed through and held by the second block, the first and second optical fibers are opposed to each other while the microfilm is placed between the end faces in different positions in the film width direction;

a light source for guiding light to said first optical fibers;

a photosensor for detecting a quantity of light incident on said second optical fibers;

a binarizing section for binarizing an output of the photosensor; and a searching section for determining the presence of frames based on binarized signals to perform frame search;

wherein end portions of said first optical fibers are bunched on the side of said light source, and a bunched portion are detachably and non-rotatably held relative to one lamp incorporated in said light source.

Specifically, in the present invention, one lamp is sufficient as the light source for guiding light to each optical fiber, and the device can be compact as compared with a device in which each optical fiber has a corresponding separate lamp. Moreover, since the position of the end face of each optical fiber of the bunched portion relative to the lamp does not vary after the disassembly, inspection or maintenance of the device, the quantity of light guided to each fiber can maintained at constant or the same, so that the frame detection accuracy can be enhanced.

As the lamp for guiding light to the bunched optical fibers, a lamp as a light source for image projection can be used. Preferably, the bunched portion is inserted through and fixed in a substantially cylindrical plug, and the plug is non-rotatably and detachably attached to a substantially cylindrical socket which is disposed coaxially with a light outlet port or small hole made in a reflection plate surrounding the lamp. The reflection plate has a substantially box shape to surround the lamp. It is also preferred that light from the lamp is prevented from directly entering the optical fibers by placing a shielding plate between the lamp and the small hole.

According to another aspect, the present invention provides a microfilm search device for distinguishing presence of frames from a density change in a running direction of a microfilm and searching for a desired frame from the microfilm, comprising:

a pair of blocks arranged across the microfilm in a width direction and opposed to each other with placing the microfilm therebetween;

a plurality of optical fibers whose end faces passed through and held by the blocks are opposed to each other while the microfilm is placed between the end faces;

a light source for guiding light to the optical fibers held by one block;

a photosensor for detecting a quantity of light incident on the optical fibers held by the other block;

a binarizing section for binarizing an output of the photosensor; and a searching section for determining the presence of frames based on binarized signals to perform frame search;

wherein each of said blocks is formed of a metal plate exposed to a surface opposite to the microfilm and a resin integrally molded on a back side of the metal plate, and a surface of said metal plate being abraded and polished.

In the aspect, surfaces, which abut on the film, of the metal plates of the blocks for holding the optical fibers whose end faces are opposite to each other with the microfilm being placed therebetween can be smoothed, and provided with a sufficient hardness. There is no possibility of damaging the film. Moreover, since the optical fiber end faces are abraded or burnished together with the metal plate surfaces, the optical fiber end faces do not protrude from the metal plate surfaces and fail to scratch on the film. Therefore, the film is prevented from contacting and damaging the optical fiber end faces, and there is no possibility of deteriorating the light incidence/emission efficiency. Since the metal plate has a conductivity, it is suitable for preventing the film from being electrified.

The metal plate may be of a stainless steel, and the resin may preferably be prepared by mixing glass fiber in polybutylene terephthalate (PBT). In this case, by setting the linear expansion coefficients of the metal plate and the resin substantially the same, the blocks can be prevented from being thermally deformed. When the metal plates of the blocks are electrically connected to each other to the same electric potential, and grounded, the electrification by static electricity and the generation of electrostatic noises can securely be prevented.

BRIEF DESCRIPTION OF THE INVENTION

FIG. 5 is a diagram showing an arrangement of main parts of the microfilm search device of the embodiment and explaining an flow of operation according to the present invention;

FIGS. 6A, 6B and 6C are explanatory views of arrangement of optical fibers which serve as photosensors or density sensors on microfilms, and show tracking loci of the photosensors relative to microfilms recorded in Simplex, Duplex and Duo systems, respectively;

DETAILED DESCRIPTION OF THE PREFERRED EMBODIMENT

Figure 1:
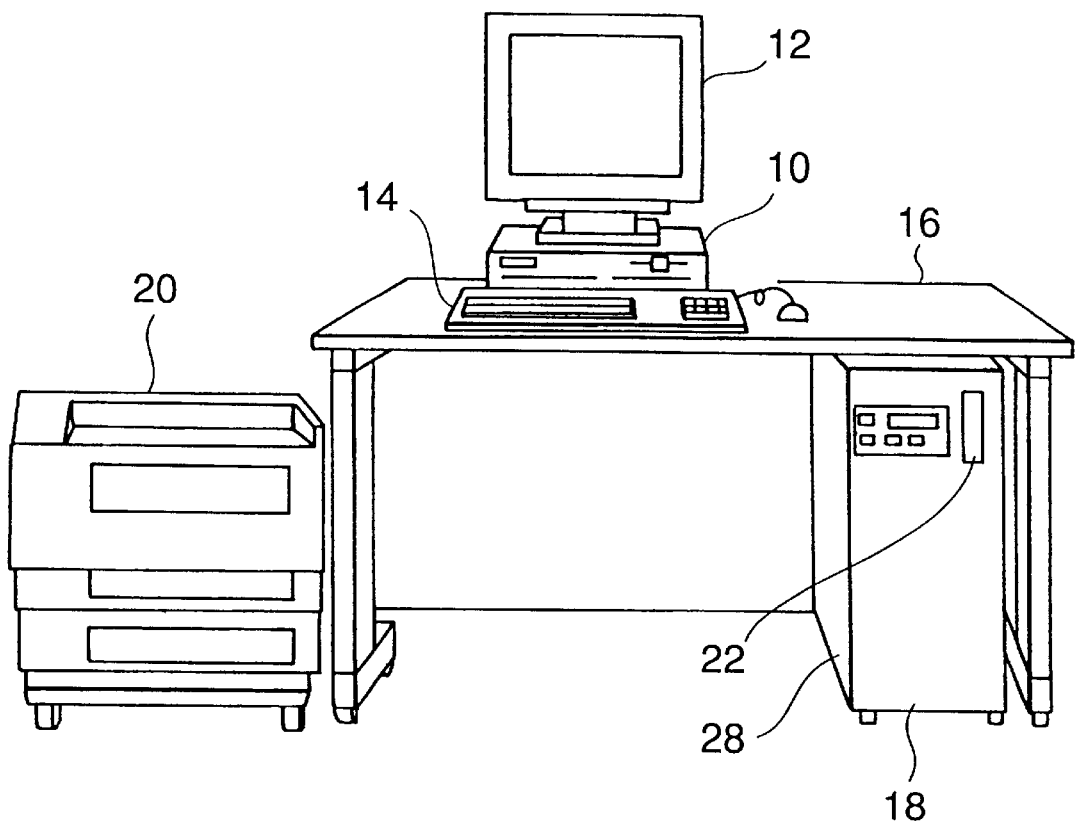
FIG. 1 is a diagram showing an image reading and processing apparatus which incorporates a microfilm search device of an embodiment of the present invention.

In FIG. 1, a reference numeral 10 denotes a computer body containing a CPU or other processing means. Display means 12 such as a CRT or a liquid crystal panel and a keyboard 14 are placed on a desk 16. A scanner 18 is stored under the desk 16 and incorporates therein a microfilm search device according to the present invention. Numeral 20 denotes a printer placed beside the desk 16.

The scanner 18 has a cartridge insertion port 22 formed in the upper portion of its front panel. The scanner 18 reads, at a low resolution, an image on a roll of microfilm 26 with a width of 16 mm held in a cartridge 24 (refer to FIGS. 2 and 3) which is loaded through the insertion port 22. The CPU in the computer body 10 performs a predetermined image processing of the read image, and the resultant image is displayed on the display means 12.

The reading or scanning operation of the image is carried out while the roll film 26 moves without moving a line sensor 96, which will be described hereinafter in details. During the operation, the CRT display device 12 sequentially changes and displays the read image synchronously with the travel of the film 26. Therefore, the displayed image moved in the display surface of the CRT 12 is in synchronization with the travel of the film 26, so that the displayed image may be substantially the same as that which is projected on a screen.

For a manual search, an operator monitors the image on the display means 12 and instructs a print output of a required image on the display means 12. In response to this output instruction, the scanner 18 sets a corresponding frame in the correct position, and reads the entire image on the frame at a high resolution. The high density image is printed by the printer 20, and either stored in an optical magnetic disk, a hard disk or the like, or transferred to an external processing device.

For an automatic search, the address of a desired frame is input through the keyboard 14. In the automatic search, as aforementioned, the frames on the microfilm 26 are detected, and the number of the frames is counted to search for a desired frame. The frame search is performed by the searching section 116 using the determination results of the determination section 112 indicating the presence of frames.

The structure of the scanner 18 will now be described. The scanner 18 has a vertically longitudinal casing 28, in which there are arranged a feed reel driving unit 30 in the upper potion of the front side and a take-up reel driving unit 32 at the lower portion of the front side. When the cartridge 24 is inserted into the cartridge insertion port 22, the cartridge 24 is moved automatically so that a reel 24A held in the cartridge 24 engages with a rotating shaft of the feed reel driving unit 30. And then, the feed reel driving unit 30 pulls out the leader portion of the roll film 26 from the cartridge, 24 and feeds it downward to guide it to a take-up reel 32A in the take-up reel driving unit 32.

Figure 2:
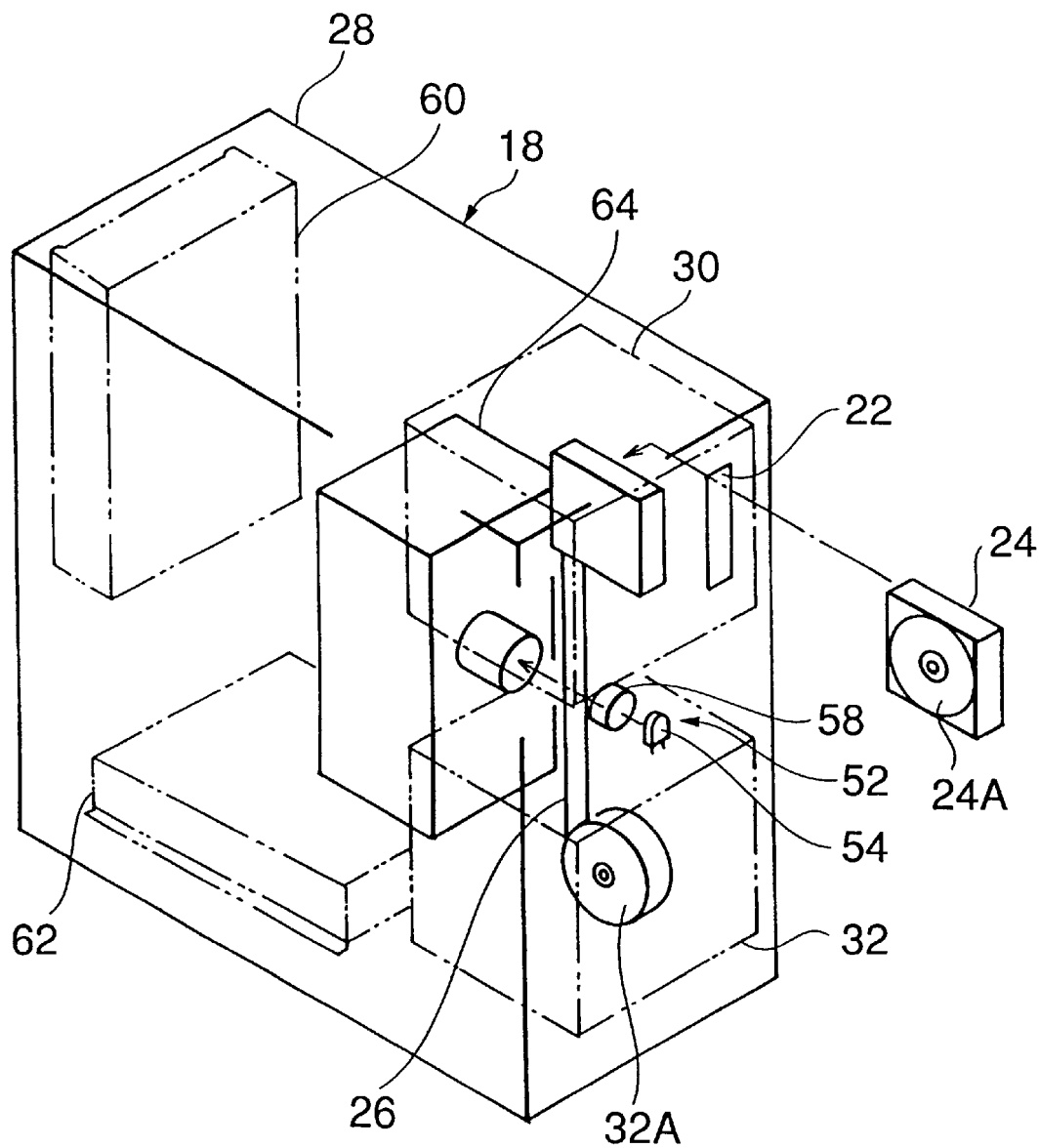
FIG. 2 is a perspective view illustrating the interior of a scanner used in the embodiment of FIG. 1.
Figure 3:
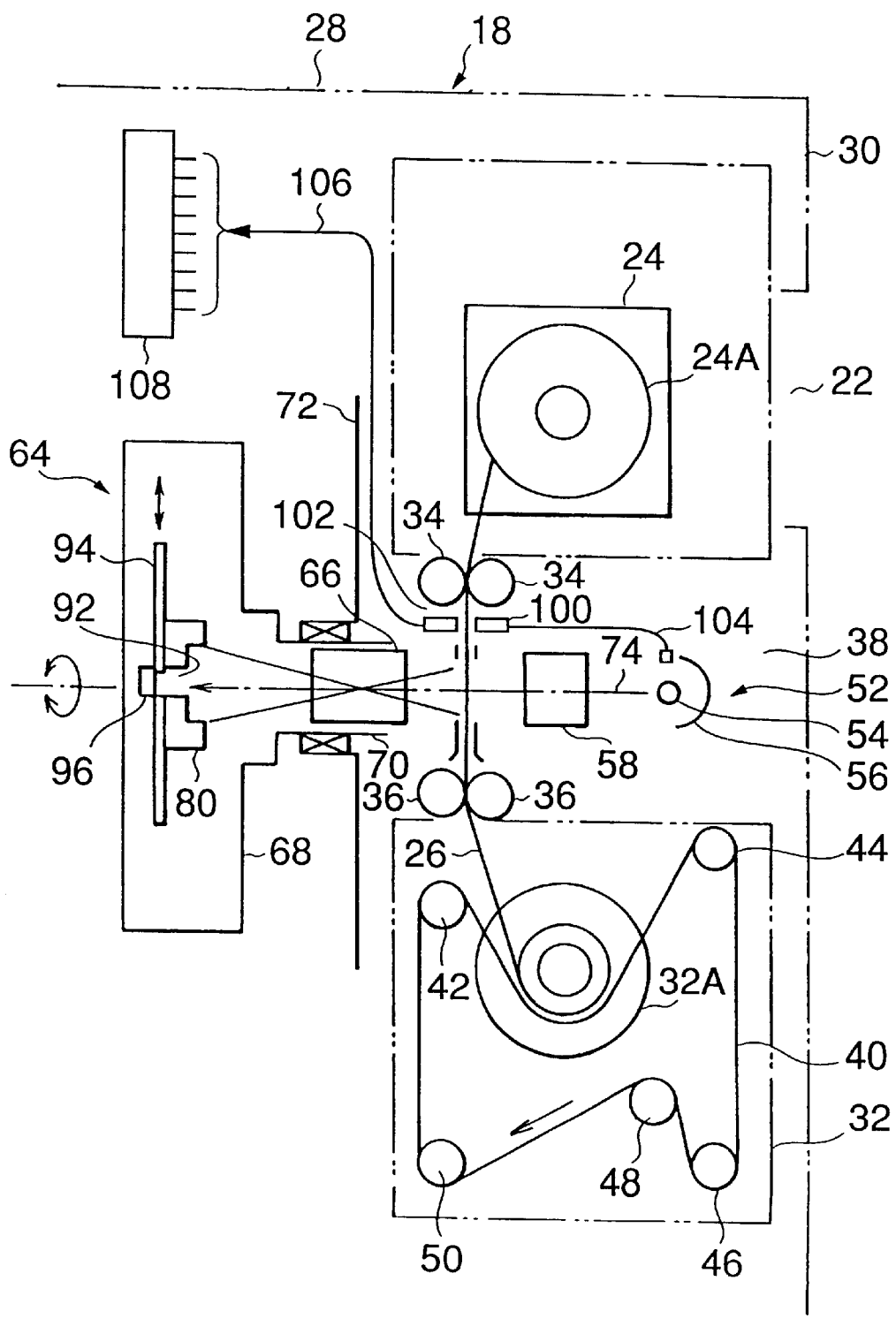
FIG. 3 is a side view illustrating an arrangement of main parts of the scanner shown in FIGS. 1 and 2.

When viewing the scanner 18 in FIGS. 2 and 3, the film 26 passes through the rear side of the open space between the reel driving units 30, 32, that is, the film 26 passes through at the inner back side viewed from the front of the casing 28. Referring to FIG. 3, there are shown guide rollers 34, 34, 36 and 36 for guiding the film 26. Accordingly, a space 38 is defined by the open area between the reel driving unit 30, 32 and a front panel 28A of the casing 28, and a light source 52, which will be described later, is housed in this space 38.

The take-up reel driving unit 32 has a drive belt 40 which travels while contacting the reel 32A as shown in FIG. 3. The drive belt 40 is wound on guide rollers 42 and 44, a drive roller 46, an encoder 48 and a tension roller 50, and it is driven by the drive roller 46 in a film take-up direction (indicated by an arrow in FIG. 3). The encoder 48 detects the feeding amount of the film 26 and outputs a sampling signal every time a constant feeding amount of the film 26 (e.g., 0.1 mm) is reached. The sampling signal functions as a clock signal to instruct a sampling timing for sampling and simultaneously binarizing the density signal, which is an output of a photosensor 108, as described hereinafter in details.

The light source 52 for projecting an image on the microfilm 26 is housed in the space 38 between the above-described reel driving units 30, 32, and includes a lamp 54, a reflection mirror 56, a condenser lens 58, an appropriate filter. In FIG. 2, a power supply circuit 60 and a power control circuit 62 for controlling an actuator such as a motor are illustrated.

Figure 4:
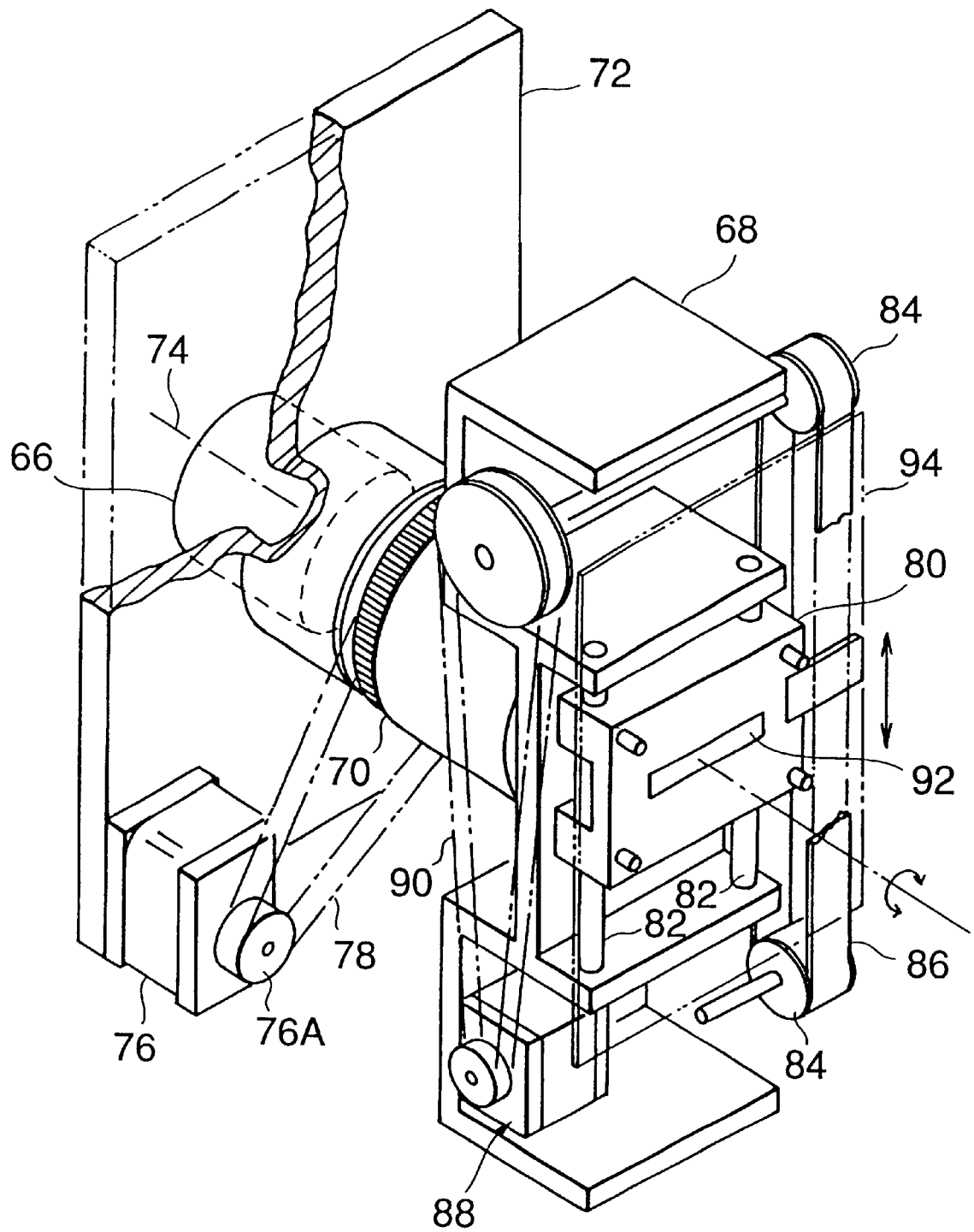
FIG. 4 is a perspective view illustrating a line sensor unit in the scanner of FIG. 3.

A line sensor unit 64 will now be described. The line sensor unit 64 is integrated with a projection lens 66. More specifically, as shown in FIGS. 3 and 4, a cylindrical portion 70 for holding the projection lens 66 is integrally formed with a frame (rotatable frame) 68 of the line sensor unit 64. The projection lens 66 mounted in the cylindrical portion 70 is a fixed focus lens with a magnifying power of approximately two. The cylindrical portion 70 is rotatably supported by a frame (fixed frame) 72, which is secured to the casing 28, so that the inclination of an image to be read can be corrected. The cylindrical portion 70 rotates about a light axis 74 perpendicular to the surface of the film 26.

A belt 78 is wound around the cylindrical portion 70 of the rotary frame 68 and a pulley 76A of a servo motor 76 mounted on the fixed frame 72. As the servo motor 76 rotates, the rotary frame 68 rotates around the light axis 74.

On the rotary frame 68, a movable plate 80 is provided on the side opposite to the cylindrical portion 70 as shown in FIG. 4. The movable plate 80 is slidably mounted on a pair of guide rods 82, 82 to permit the movable plate 80 to reciprocate in the vicinity of an opening of the cylindrical portion 70 in a direction perpendicular to the light axis 74.

In the rotary frame 68, a belt 86 wound on pulleys 84, 84 extends in a direction parallel to the up-and-down moving direction of the movable plate 80, and one side of the movable plate 80 is fixed to the belt 86. The rotation of a servo motor 88 is transmitted via a belt 90 to one of the pulleys 84. With this structure, when the servo motor 88 rotates forward and in reverse, the movable plate 80 reciprocates across a plane perpendicular to the light axis 74.

On the movable plate 80, an elongated window (narrow slit) 92 is formed in a direction perpendicular to the guide rods 82, 82, i.e., in a direction perpendicular to the up-and-down moving direction of the movable plate 80. The window 92 has its longitudinal center that corresponds with the light axis 74. A printed circuit board 94 is fixed to the rear face of the movable plate 80, i.e., the face opposite to that facing the cylindrical portion 70, so as to be perpendicular to the light axis 74.

A longitudinal CCD arrayed line sensor 96 is fixed to the board 94 to face the window 92 (FIG. 3). In addition, a preamplifier for amplifying the output of the line sensor 96 is mounted on the board 94. The positioning of the light reception face of the CCD line sensor 96 must correspond to a plane on which an image projected from the projection lens 66 is focused.

A frame detecting device will next be described with reference to FIG. 5. In a position in front of the position where an image on the microfilm 26 is read, i.e., on the upstream side of the light axis 74 (the side of the feed reel 24A), a pair of optical fiber holding blocks 100, 102 are provided in such a manner that they extend across the film 26 along the width direction and they are opposed to both faces of the film 26 with slight gaps. Optical fibers 104, 106, nine each being arranged in the film width direction, are inserted through the blocks 100, 102, respectively. Structures of the blocks 100, 102 will be described hereinafter in details.

The optical fibers 104, 106 are held in the blocks 100, 102, so that the optical axes of the fibers 104, 106 are perpendicular to the film 26, and end faces of the fibers 104, 106 are opposed to each other with the film 26 placed therebetween. Specifically, the end faces of nine optical fibers 104 are opposed to the end faces of nine optical fibers 106, respectively. As a result, there are nine sets of the opposed end faces with the film 26 placed therebetween.

Nine optical fibers 104 held in the block 100 are bunched and guided toward the vicinity of the lamp 54 of the light source 52. Light beams are radiated from the lamp 54 to the nine optical fibers 104, and guided to one surface (surface on the side of the block 100) of the film 26. The structure of light source 52 will be described hereinafter in details.

The light beams emitted from the nine optical fibers 104 passes through the film 26 and enters into the opposed light receiving optical fibers 106 held in the block 102. The nine optical fibers 106 are guided from the block 102 to the nine photosensors 108, respectively. Density signals outputted from the nine photosensors 108 are separately transmitted to binarizing sections 110, sampled in synchronization with a sampling signal outputted from the encoder 48, and binarized with a predetermined threshold value. The threshold value is set in accordance with a difference in density between a frame and an outer periphery of the frame.

Nine binarized signals indicating in-frame or out-frame position are transmitted to a determination section 112, in which determination results indicative of the presence of frames are obtained based on the output of each photosensor 108. A signal of a sensor selecting section 114 is also supplied to the determination section 112. The sensor selecting section 114 selects the optical fiber(s) 106 whose end face is positioned in the frame travel width corresponding to a film photographing system such as Simplex, Duplex, Duo and the like, and the photosensor(s) 108 connected to the selected optical fiber(s) 106. The determination section 112 selects only the determination result(s) of the sensor(s) 108 selected by the sensor selecting section 114 from nine determination results in accordance with the corresponding photographing system.

The end faces of the optical fibers 104, 106 are, as shown in FIG. 6A, positioned on a straight line L perpendicular to the running direction of the film 26 and in different positions along the width direction of the film 26. In the embodiment, since the photosensor 108 detects the quantity of incident light of the optical fiber 106, the photosensor 108 is substantially positioned in a position where the end face of the optical fiber 106 is opposed to the film 26. Therefore, FIG. 6A represents that the photosensors 108 are positioned in end face positions of the optical fibers 106 on the side of the film 26.

The nine photosensors 108 are positioned along the film width direction in such a manner that a plurality of photosensors 108 constantly pass through one frame even if the film photographing system differs. FIG. 6A shows a case where frames of a microfilm photographed in Simplex system are detected. In this case, the determination section 112 detects frames using eight photosensors 108A selected by the sensor selecting section 114, and detects blips 118 with another photosensor 108B. Accordingly, the determination section 112 determines the presence of frames using the binarized signals outputted from eight binarizing sections 110 corresponding the selected eight photosensors 108A. For example, when more than half or more than a constant ratio of the determination results obtained by each photosensors 108A represent black (in-frame portion of a negative film), it is determined that there is a frame. Determination of frames may be performed using a logical product or a logical sum of the determination results at the each position of the photosensor 108. Moreover, in this case, search may be performed using the output of the photosensor 108B for detecting the blips 118.

FIG. 6B shows a case of Duplex system. Since a front face and a back side face of an original document are simultaneously photographed on upper and lower channels of the film, between the channels disposed is a photosensor 108C which does not detect frames. In this case, based on the output of the sensor selecting section 114, the determination section 112 detects frames in each channel using outputs from three photosensors 108D and three photosensors 108E extending in widths of the upper and lower channels, respectively, except an output from the photosensor 108C.

FIG. 6C shows a case of Duo system, and a center photosensor 108F does not detect frames. Therefore, based on the output of the sensor selecting section 114, the determination section 112 detects frames in each channel with four photosensors 108G and four photosensors 108H included in upper and lower groups, respectively. The searching section 116 searches for a desired frame by counting determination signals outputted by the determination section 112.

Figure 7A:
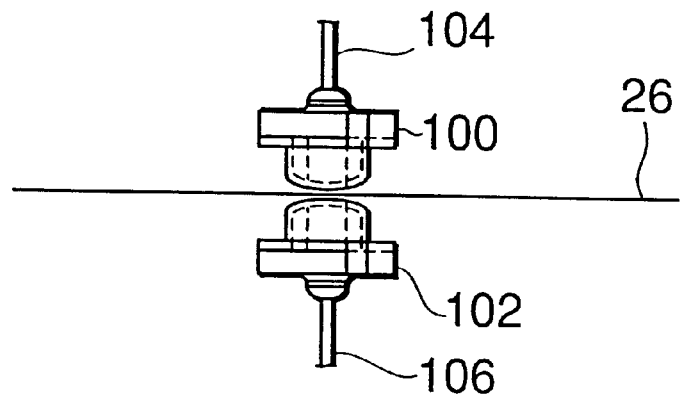
FIGS. 7A and 7B are a side view and a bottom view showing a combined state of opposite optical fiber holding blocks.
Figure 7B:
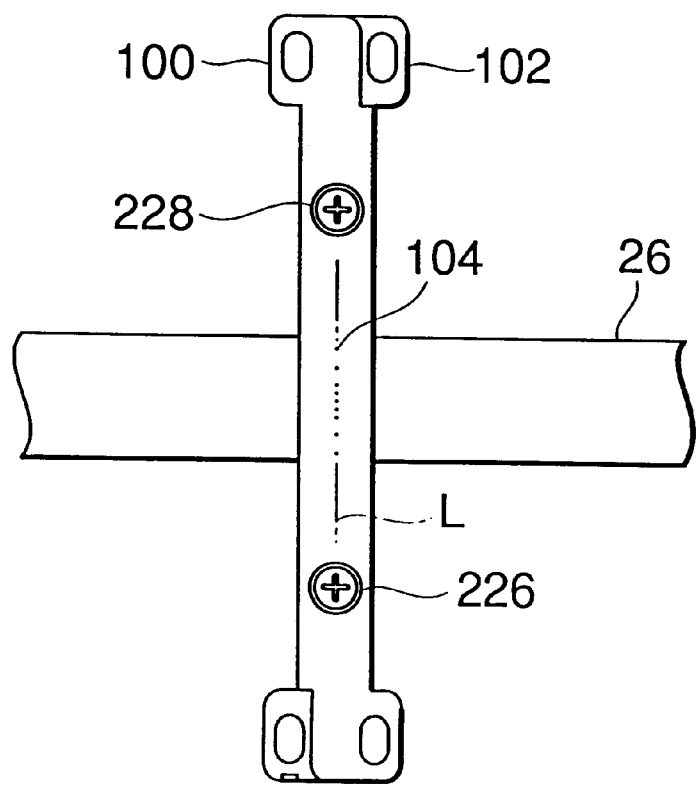
Figure 8:
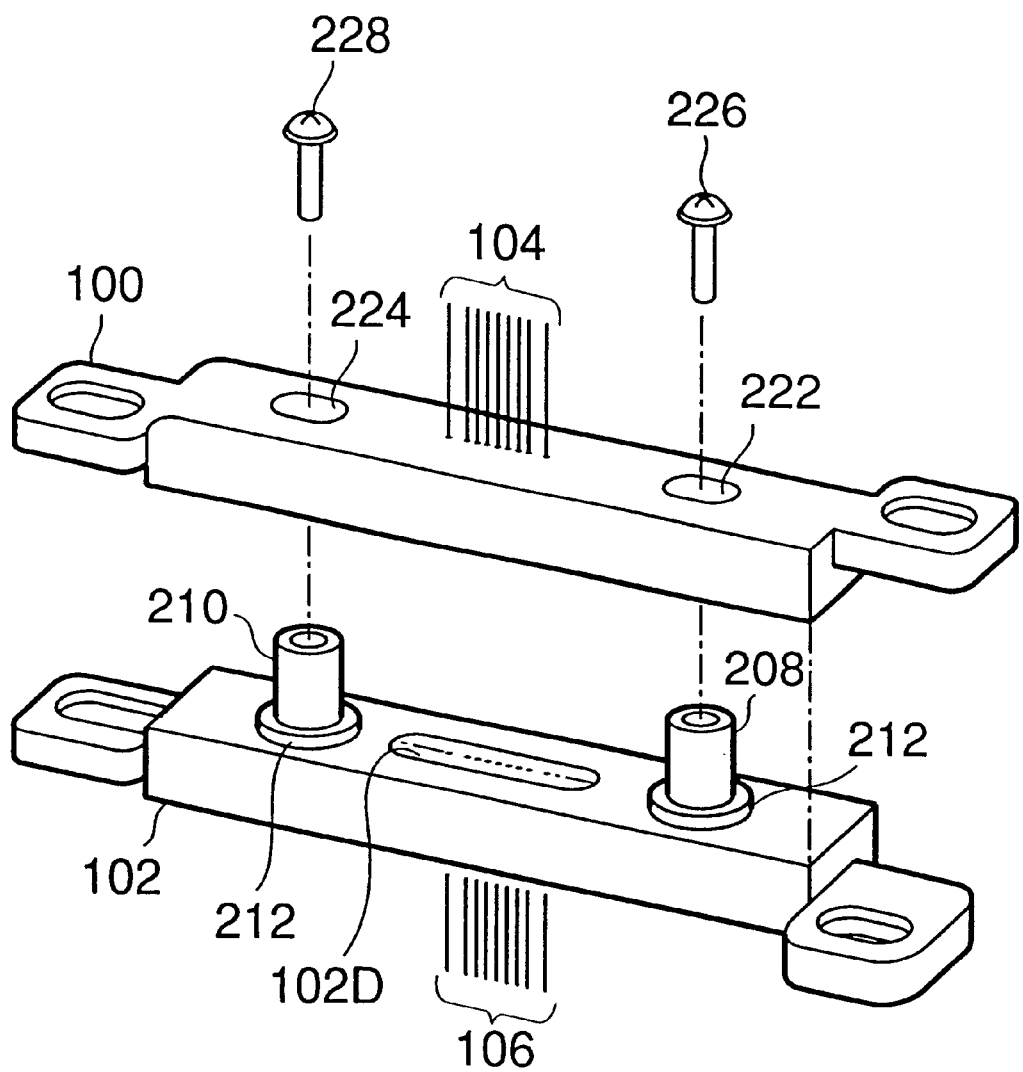
FIG. 8 is an exploded perspective view of the optical fiber holding blocks.
Figure 9:
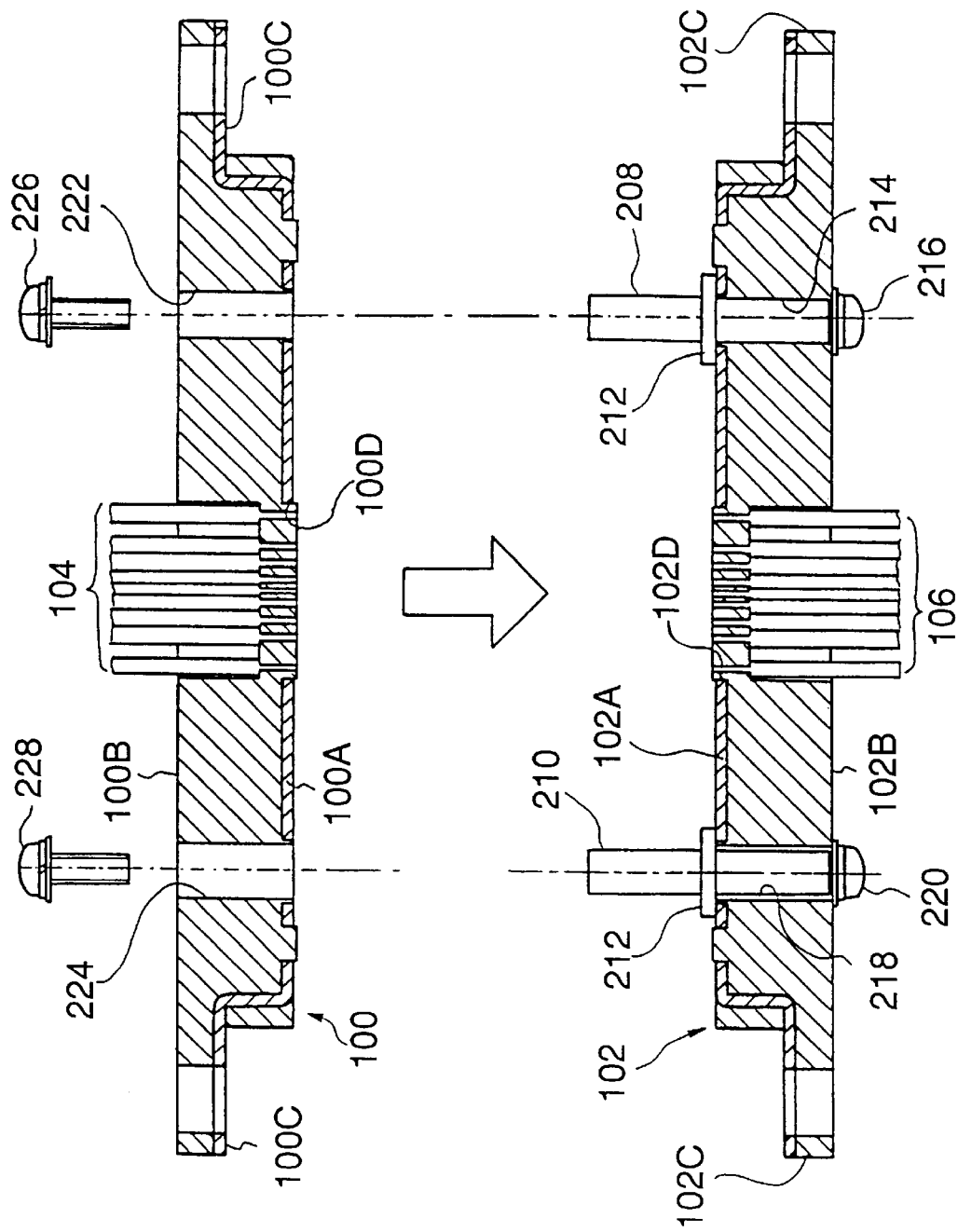
FIG. 9 is an exploded sectional view of the optical fiber holding blocks.

The optical fiber holding blocks 100, 102 for holding the ends of the optical fibers 104, 106, respectively will next be described with reference to FIGS. 7 to 10. FIGS. 7A and 7B are a side view and a bottom view showing a combined state of the blocks 100, 102; FIG. 8 is an exploded perspective view of the blocks; FIG. 9 is an exploded sectional view of the blocks; and FIG. 10 is an enlarged sectional view of the block showing a vicinity of a portion for holding one end of the optical fiber.

The blocks 100, 102 having the same structures are reversed to each other, and combined for use. Specifically, opposite faces of the blocks 100, 102 are formed by metal plates 100A, 102A of stainless or the like, respectively. Behind the metal plate 100A, 102A, a synthetic resin 100B, 102B formed by mixing about 30 wt % of glass fiber in polybutylene terephthalate (PBT) is integrally molded. Opposite ends of the metal plate 100A, 102A and the resin 100B, 102B are extended to form lug portions 100C, 102C to be attached to a device frame (not shown), respectively. The attachment portions 100C, 102C are deviated in the width direction of the respective block 100, 102. Therefore, when the blocks 100, 102 are combined and attached to the device frame (refer to FIG. 7B), a screw-driver or another tool can be prevented from interfering with the one of attachment portions 100C, 102C.

The nine optical fibers 104, 106 are held with predetermined intervals on the straight line L (refer to FIGS. 6A, 7B) in the center of the block 100, 102 in the longitudinal direction, respectively. The optical fibers 104, 106 are covered with resins 202 as shown in FIG. 10. The resin 202 on one end of each fiber 104, 106 is peeled off and exposed by a predetermined length. The exposed portion of each fiber 104, 106 is passed through a holding hole 204 formed in each block 100, 102, and fixed to the block 100, 102 by an adhesive agent 206. The end faces of the optical fibers 104, 106 are abraded, polished and flattened together with the surfaces of the blocks 100, 102, respectively.

Figure 10:
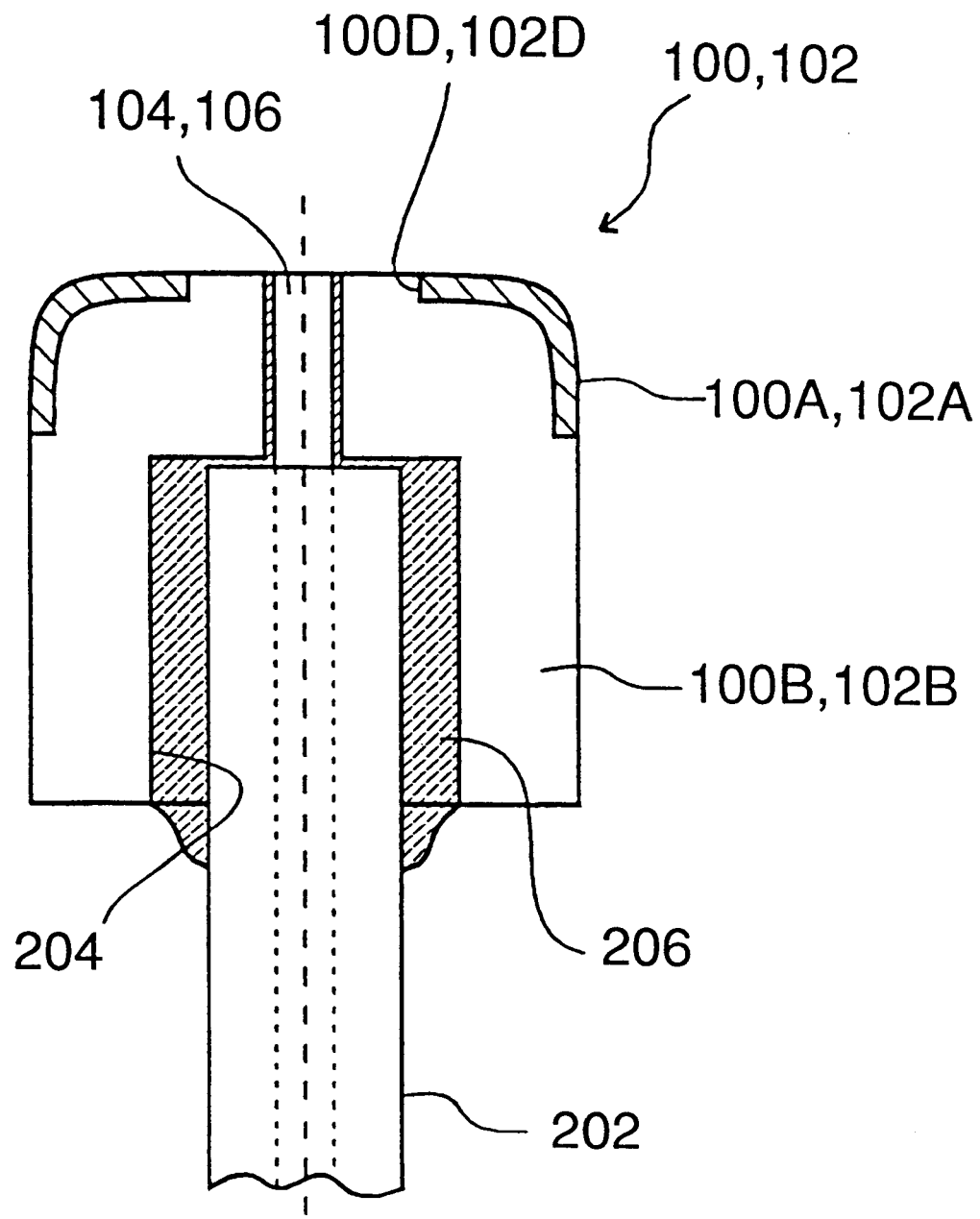
FIG. 10 is an enlarged sectional view showing a vicinity of an optical fiber holding portion of the block.

As shown in FIG. 10, opposite edges of the face of the metal plate 10A, 102A facing the block 100, 102 are abraded and smooth polished in circular arc shapes. Moreover, an elongated opening 100D or 102D is formed around the center of the metal plate 100A or 102A to surround the end faces of the optical fibers 104 or 106 (FIGS. 8, 9, 10). The opening 100D, 102D surrounding the end faces of the fibers 104, 106 are filled with the resins 100B, 102B, respectively. Accordingly, by abrading and polishing the surfaces of the metal plates 100A, 102A, the metal plates 10A, 102A, the resins in the openings 100D, 102D and the end faces of the optical fibers 104, 106 are positioned on the same plane, and can be flattened smooth, respectively.

For the block 102, a positioning reference pin 208 and a connecting pin 210 are fixed in positions as apart as possible in a block longitudinal direction. The pin 208 or 210 is tubular, and has internal threads at opposite ends and a flange 212 in its longitudinal center. The reference pin 208 is inserted into a circular hole (reference hole) 214 formed in the metal plate 102A and the resin 102B of the block 102 from the side of the metal plate 102A, and fixed to the block 102 by inserting a screw 216 from the side of the resin 102B (FIG. 9).

Similarly, the connecting pin 210 is temporarily fixed by a screw 220 in a hole 218 formed long in the longitudinal direction of the block 102 in the metal plate 102A and the resin 102B. For the other block 100, there are formed a circular reference hole 222 to which the reference pin 208 is fixedly inserted, and a hole 224 which is long in the longitudinal direction of the block 100 and to which the connecting pin 210 is loosely inserted.

With such construction, at the time of mounting the block 100 to the block 102, first the reference pin 208 fixed to the block 102 is engaged in the reference hole 222 of the block 100, and concurrently the temporarily fixed connecting pin 210 is engaged in the long hole 224, while the blocks 100 and 102 are combined. Subsequently, the screws 226 and 228 are inserted and tightened to the pins 208 and 210 from the side of the block 100, and the screw 220 of the connecting pin 210 is concurrently tightened from the side of the block 102.

In this case, the flanges 212 attached to the pins 208, 210 are formed of conductive materials. Accordingly, the flanges 212 not only function to keep constant a gap dimension between the blocks 100 and 102, but also serve to electrically connect the metal plates 100A, 102A to keep them in the same electric potential. By connecting the attachment portions 100C and 102C to the device frame, the metal plates 100A and 102A are grounded.

As aforementioned, since the blocks 100 and 102 are positioned by the reference pin 208 in the block width direction and by the connecting pin 210 in the block longitudinal direction, light axes of the optical fibers 104, 106 of the blocks 100, 102 can be aligned and held with high precision. Moreover, by loosening the screws 216, 220 or 226, 228 of the pins 208, 210, the blocks 100, 102 can easily be disengaged, and by cleaning the end faces of the optical fibers 104, 106, dirt can be removed.

Additionally, the reference holes 214, 222 and the long connection holes 218, 224 of the blocks 100, 102 can be processed as follows:

In one method, the blocks 100 and 102 are set to a separate jig, and fixed while the light axes of the optical fibers 104 and 106 are aligned. Subsequently, the reference holes 214 and 222 or the long connection holes 218 and 224 are simultaneously formed through the blocks 100 and 102 by drill processing. In another method, the blocks 100 and 102 are formed in one common metal mold by integrating the sides of the resins 100B and 102B, and the reference holes 214 and 222 and the long connection holes 218 and 224 are simultaneously formed by drill processing. Subsequently, the resin portion is divided with a cutter. Alternatively, the metal plates 100A or 102A may be formed in a cylindrical shape, and filled with resin.

In the embodiment, since the block 100 or 102 is formed by integrally molding the stainless metal plate 100A or 102A with the PBT resin 100B or 102B, deformation by temperature change does not easily occur. Moreover, since the metal plates 100A and 102A are exposed on the faces to be opposed to the film 26, the film 26 can be prevented from being electrified by grounding the metal plates 100A and 102A to the device frame.

A light source for guiding light to the optical fibers 104 will next be described with reference to FIG. 11. In the embodiment, the light source 52 for image projection is also used as the light source for guiding light to the optical fibers 104. Specifically, the light source of the optical fibers 104 is constituted of the image projecting light source 52 which is provided with the lamp 54, a shielding plate 56A for shielding the optical fibers 104 from light beams directly radiated from the lamp 54, and the reflection plate 56' for guiding light beams reflected by the lamp 54 to the optical fibers 104.

Figure 11:
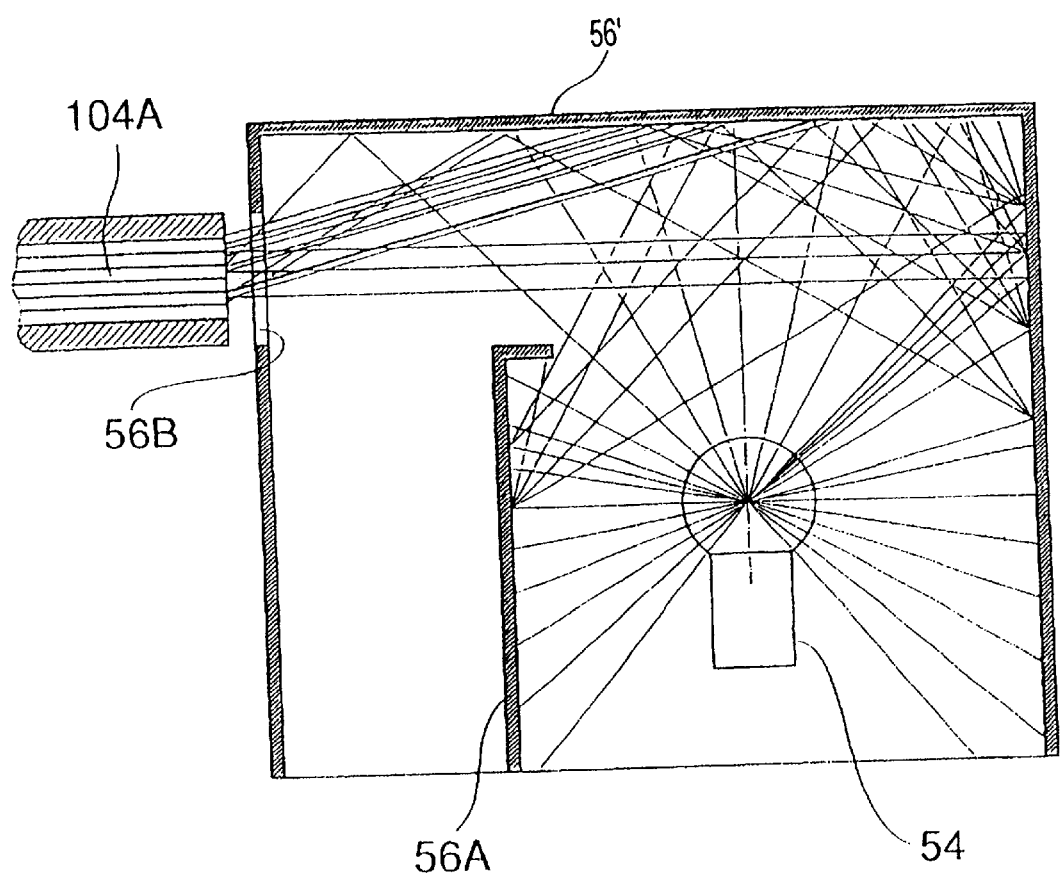
FIG. 11 is a sectional view showing an embodiment of a light source.

The reflection plate 56' has a box-like construction mi surrounding the lamp 54, as shown in FIG. 11, and a small hole 56B through which light beams can emit outside is formed in one wall of the box. That is, the small hole 56B serves as a-light emission or outlet port. Ends of nine optical fibers 104 are bunched, and a bunch 104A is held in such a manner that an end face of the bunch faces to the inside of the box-shaped reflection plate 56' from the outside of the small hole 56B. The shielding plate 56A also prevents the light beams of the lamp 54 from being directly radiated to the small hole 56B in the box.

Figure 12:
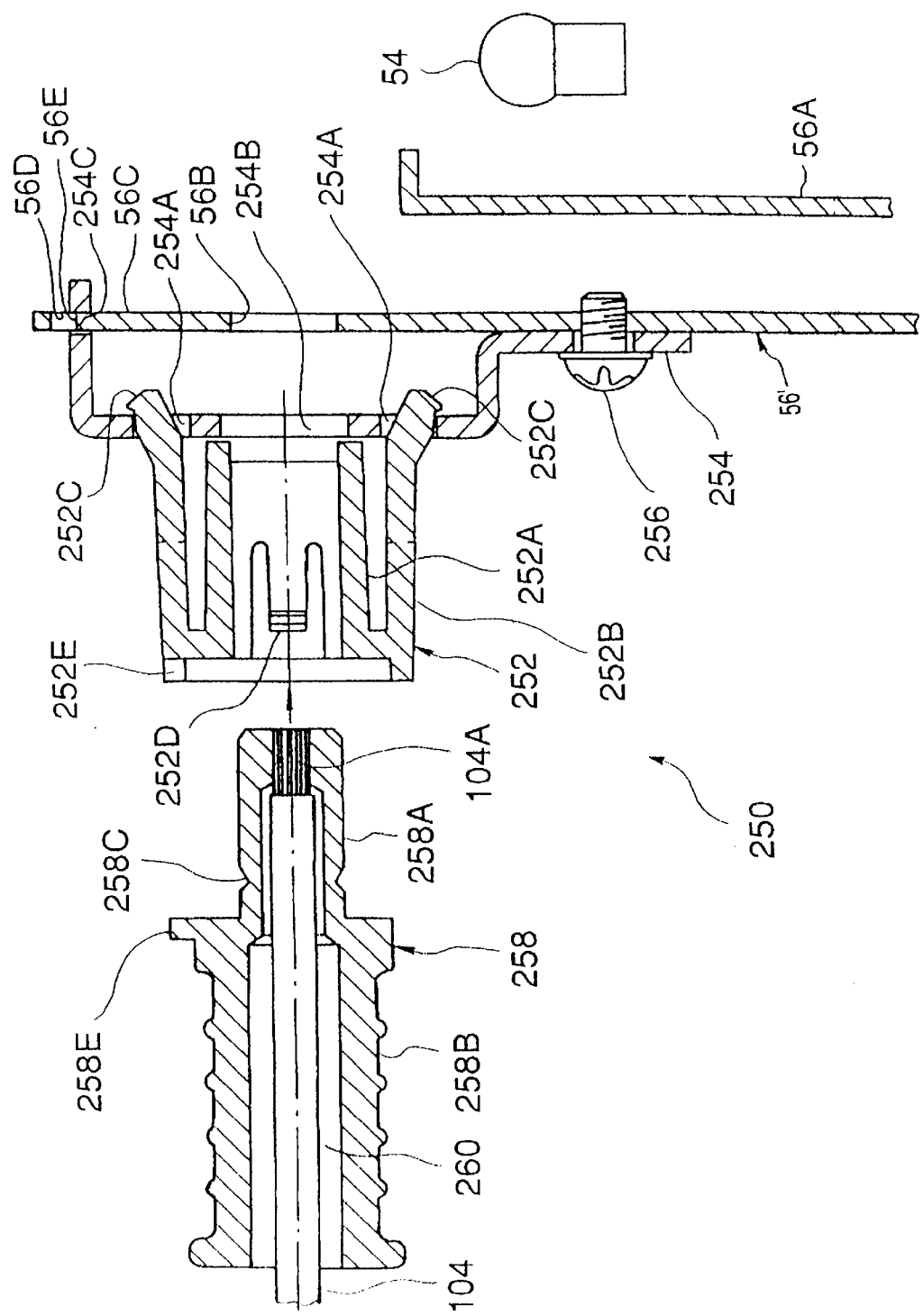
FIG. 12 is a sectional view showing an attachment structure of an optical fiber bunched portion.
Figure 13:
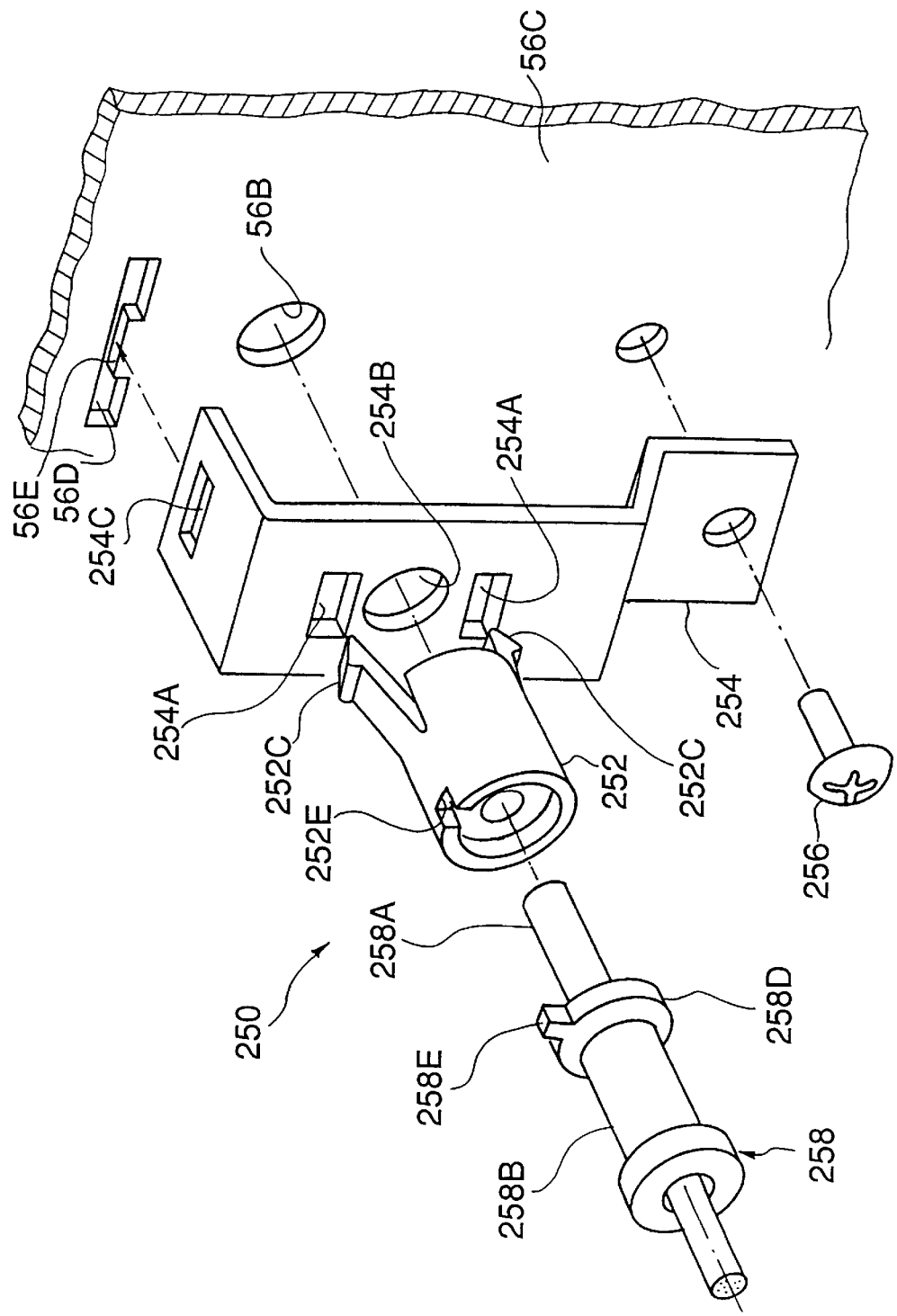
FIG. 13 is an exploded perspective view of the attachment structure of FIG. 12.

An attachment structure 250 for holding the bunch 104A of the optical fibers 104 relative to the reflection plate 56' of the light source 52 will be described. FIG. 12 is a sectional view showing main parts of the attachment structure 250, and FIG. 13 is an exploded perspective view thereof. In FIGS. 12 and 13, numeral 252 denotes a substantially cylindrical socket, and the socket 252 is attached to an outer wall 56C of the box-shaped reflection plate 56' by a socket holder 254.

As shown in FIG. 12, the socket 252 is formed by integrally molding an inner cylinder 252A and an outer cylinder 252B, and attached to the socket holder 254 by engaging a pair of clicks 252C, 252C formed on the outer cylinder 252B into engagement slots 254A, 254A formed in the socket holder 254. In this case, the socket 252 is attached perpendicular to the socket holder 254, and the inner cylinder 252A is positioned coaxially with a small hole 254B formed in the socket holder 254 (FIG. 13).

The socket holder 254 is formed by bending the upper portion of a flat plate perpendicularly and bending the lower portion thereof into a crank shape. After a square hole 254C formed in the upper portion of the socket holder 254 is advanced into a window 56D formed in the outer wall 56C, the socket holder 254 is entirely pushed downward until a click 56E protruded from a lower edge of the window 56D is engaged in the square hole 254C. Additionally, the lower portion of the socket holder 254 is brought in contact with the outer wall 56C, and fixed to the outer wall 56C by a screw 256. In this case, the socket 252, the small hole 254B and the small hole 56B are positioned along the same axis.

A plug 258 is detachably attached to the socket 252 which is attached to the outer wall 56C as aforementioned. The plug 258 has a substantially cylindrical configuration, its tip end forms a small-diameter insertion portion 258A, and its other end forms a large-diameter grip portion 258B. The bunch 104A of the optical fibers 104 is inserted into the plug 258 from the side of the grip portion 258B, and fixed by filling a space 260 with an adhesive or bonding agent.

The end face of the bunch 104A of the optical fibers 104 is exposed from a tip-end face of the insertion portion 258A, and flattened and smoothed down. The insertion portion 258A is inserted and detachably and non-rotatably held in the inner cylinder 252A of the socket 252. Specifically, an annular groove 258C is formed in the outer periphery of the insertion portion 258A, while at least one click 252D which tends to be restored toward the inner-diameter direction is formed on the inner peripheral face of the inner cylinder 252A of the socket 252. By engaging the click 252D into the annular groove 258C, the plug 258 is detachably held.

A flange 258D is formed at the boundary between the grip portion 258B and the insertion portion 258A and has one protrusion 258E at the outer periphery thereof. On the other hand, a recess or concave portion 252E is formed in the socket 252 with which the protrusion 258E is engaged when the plug 258 is inserted. Therefore, when the plug 258 is inserted into the socket 252 so that the click 252D is engaged in the annular groove 258C, the protrusion 258E is engaged in the concave portion 252E to restrict the rotation of the plug 258.

Therefore, a part of light emitted from the lamp 54 is guided to the film 26 through the condenser lens 58 to form the image projecting light as aforementioned, and another part of light from the lamp 54 is reflected by the box-shaped reflection plate 56' to pass through the small holes 56B and 254B, and then enters into the optical fibers 104. In this manner, since the light reflected by the reflection plate 56' enters the optical fibers 104, an optical path length between the end faces of the optical fibers 104 and the lamp 54 is lengthened. The lamp 54 is positioned substantially far from the end faces of the optical fibers 104. The light of the lamp 54 is repeatedly reflected in a complex manner inside the reflection plate 56' before entering the optical fibers 104. As a result, light beams incident upon the optical fibers 104 are equalized to become close to parallel beams.

Moreover, since the plug 258 to which the bunch 104A of the optical fibers 104 is fixed is non-rotatably held relative to the socket 252, the plug 258 is positioned constant in a rotary direction when the plug 258 is reassembled after pulled from the socket 252 for inspection or maintenance of the device. Therefore, positions of nine optical fibers 104 in the bunch 104A relative to the lamp 54 are unchanged, and the quantity of incident light of each optical fiber 104 does not change.

Figure 14:
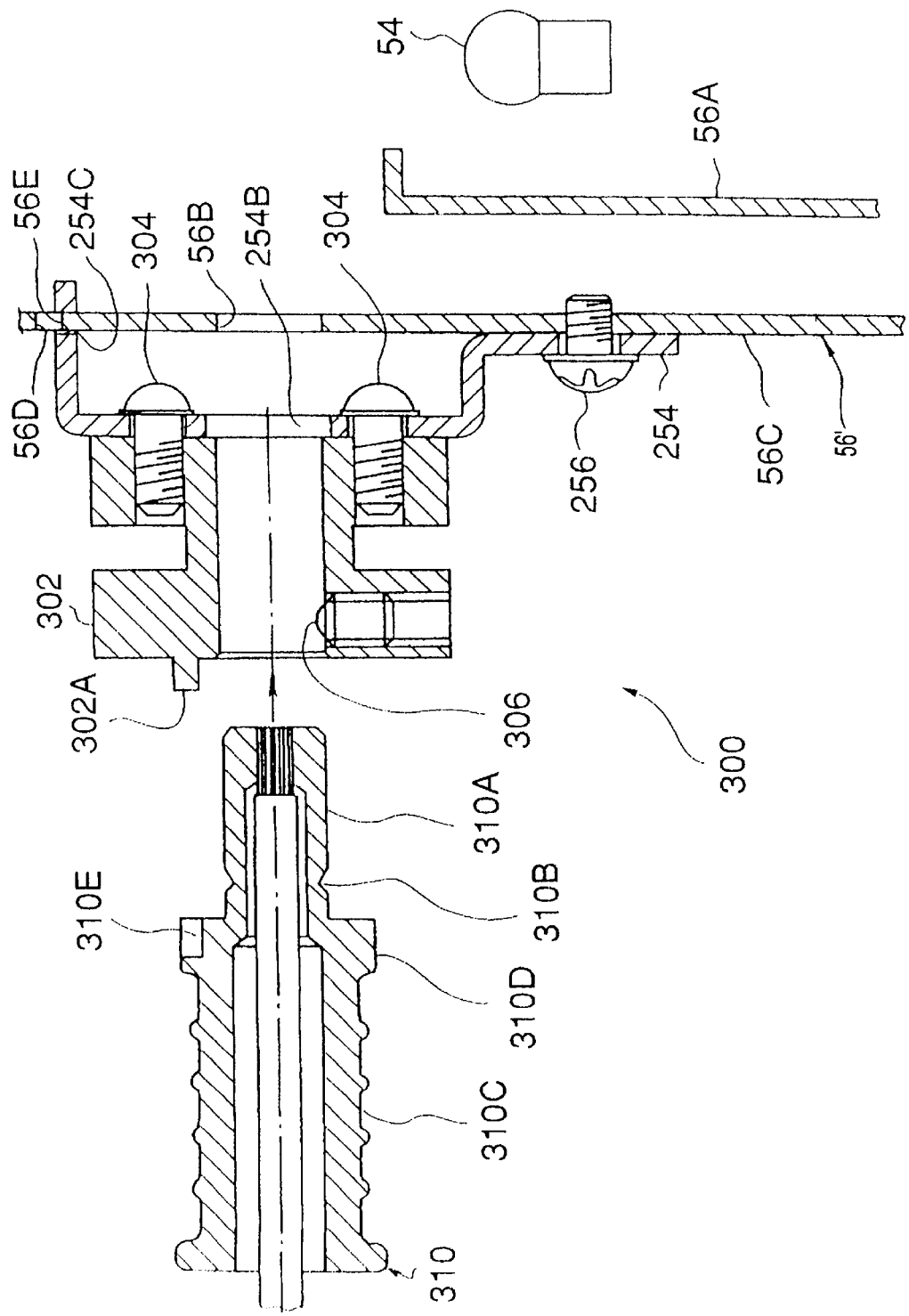
FIG. 14 is a sectional view showing another embodiment of the attachment structure of the optical fiber bunched portion.

FIG. 14 is a main-part sectional view showing another embodiment of the attachment structure for holding the optical fibers 104 onto the reflection plate 56. In an attachment structure 300, a socket 302 is fixed to the socket holder 254 with screws 304, 304, while an inner peripheral face of the socket 302 is provided with a ball plunger 306 for holding a ball which tends to be protruded in an inner-diameter direction, so that the ball is detachably engaged in an annular groove 310B formed in an insertion portion 310A of the plug 310. Moreover, a recess 310E is formed in a flange 310D of a grip portion 310C of the plug 310 in such a manner that it is engaged with a protrusion 302A formed on the socket 302.

Accordingly, the plug 310 can be detachably attached to the socket 302. At the time of attachment, the recess 310E is engaged with the protrusion 302A, so that the plug 310 is positioned in the rotary direction. Therefore, even if the plug 310 is detached/attached, the positions of the end faces of the optical fibers 104 relative to the lamp 54 are unchanged, and the quantity of incident light of each optical fiber 104 does not change. Additionally, in FIG. 14, the same section or member as in FIG. 12 is denoted by the same reference numerals, and the description thereof is not repeated.

Moreover, nine light guiding optical fibers 104 held in the block 100 have the same length. Also, nine light receiving optical fibers 106 held in the block 102 have the same length. Therefore, light attenuation conditions in each set of nine optical fibers 104, 106 are equalized, and frame detection accuracy is increased. Additionally, since the reflection plate 56' is formed into a box, the light of the lamp 54 is repeatedly reflected in the box in a complicated manner before entering the optical fibers 104. Therefore, the incident light of the optical fibers 104 is further equalized or uniformed.

In the embodiment, since the block 100 or 102 is formed by integrally molding the stainless metal plate 100A or 102A with the PBT resin 100B or 102B, the deformation by the temperature change does not easily occur. Moreover, the metal plates 100A and 102A are exposed and faces to the surface of the film 26, the film 26 can be prevented from being electrified by grounding the metal plates 100A and 102A to the device frame.

In the embodiment described above, since light is guided to each optical fiber 104 using the light source 52 for image projection or reading, the light source structure can advantageously be simplified. In the invention, however, another light source may be added for use.

In the embodiment, since the optical fibers 104 and 106 are used as aforementioned, the opposed end faces of the optical fibers 104 and 106 can be arranged adjacent to each other in the width direction of the narrow film 26. However, the present invention includes the blocks 100 and 102 each holding one optical fiber. In this case, since the binarizing section 110 directly outputs a determination signal indicative of the presence of frames, the additional determination section 112 becomes unnecessary.

Moreover, in the embodiment, since the density sensors (photosensors) are arranged on the straight line L perpendicular to the film running direction, the presence of frames can be detected at the same time. Therefore, different from a case where a plurality of density sensors (photosensors) are arranged by deviating them in the film running direction, a deviation in output timing of each density sensor (photosensor) does not need to be corrected, and a circuit structure is simplified.

According to the present invention, as aforementioned, end portions of a plurality of optical fibers are bunched on the side of the light source, and the bunched portion is detachably and non-rotatably held relative to one lamp. Therefore, one lamp is sufficient, and the device can be compact as compared with a device in which each optical fiber is provided with a lamp. Additionally, at the time of assembly, inspection or maintenance, since the position of the end face of each optical fiber in the bunched portion relative to the lamp is unchanged, the quantity of light guided to each optical fiber can be prevented from changing, and the frame detection accuracy can be enhanced.

In this case, if the image projecting lamp is also used as the light-source lamp of the optical fibers, the device can further be compactmized. The bunched portion of the optical fibers is inserted through and fixed to the plug, and the plug is detachably and non-rotatably held relative to the socket. In this structure, the plug can be easily detached/attached, which is convenient for assembly, disassembly, inspection, maintenance, and the like of the device. Furthermore, the image projecting lamp is surrounded by the box-shaped reflection plate, the end face of the bunched portion of the optical fibers is disposed opposite to the small hole as light outlet port formed in the box-shaped reflection plate, and the shielding plate is disposed between the small hole and the lamp to prevent light from being directly radiated to the optical fibers from the lamp. In this structure, the light radiated to each optical fiber can further be equalized.

Moreover, according to another aspect of the present invention, each of the blocks for holding the optical fibers whose end faces are opposed to each other with the microfilm placed therebetween is formed by the metal plate exposed to the face opposite to the microfilm and the resin integrally molded on the back side of the metal plate. Furthermore, the surface of the metal plate is flattened and smoothed down to eliminate rough or bumpy surface. The surface of the metal plate abutting on the film can be smoothed and given a sufficient hardness. Therefore, there is no possibility of damaging the film.

Moreover, since the end faces of the optical fibers and the surfaces of the metal plates are simultaneously abraded and polished to be smoothed down, the end faces of the optical fibers would not protrude from the smoothed surface of the metal plate, and therefore fail to abut on the film. There is no possibility that the end faces of the optical fibers contact or rub and damage the film. Deterioration of the light incidence/emission efficiency is avoided. Furthermore, since the metal plate has an electric conductivity, it is suitable for preventing the electrification of the film.

When the metal plate is formed of stainless steel while the resin is formed by mixing about 30 wt % of glass fiber in polybutylene terephthalate (PBT), the linear expansion coefficients of the metal plate and the resin are close to each other, and the thermal deformation of the optical fiber holding block is minimized. Moreover, by electrically connecting and grounding the metal plates of the blocks, static electricity generated in the film can securely be removed, and electrostatic noises are more suitably prevented.

What is claimed is:

1. A microfilm search device for distinguishing presence of frames from a density change in a running direction of a microfilm and searching for a desired frame from the microfilm, comprising:

a first block arranged across the microfilm in a width direction;

a second block arranged across the microfilm in the width direction, end faces of the first and second blocks being opposed to each other with the microfilm placed therebetween;

first optical fibers whose end faces pass through and are held by the first block;

second optical fibers whose end faces pass through and are held by the second block, the first and second optical fibers are opposed to each other while the microfilm is placed between the end faces in different positions in the film width direction;

a light source used in guiding light to said first optical fibers;

a photosensor for detecting a quality of light incident on said second optical fibers;

a binarizing section for binarizing an output of the photosensor; and a searching section for determining the presence of frames based on binarized signals to perform frame search;

wherein end portions of said second optical fibers are bunched on the side of said light source, and a bunched portion is detachably and non-rotatably held relative to one lamp incorporated in said light source and said bunched portion has a protrusion that engages with a box containing the lamp and preserves the relative orientation of the fibers with respect to the lamp.

2. The microfilm search device according to claim 1, wherein said one lamp is a lamp of a light source for projecting an image on the microfilm for reproduction.

3. The microfilm search device according to claim 1, further comprising:

a cylindrical socket fixed coaxially relative to a light outlet port formed in a reflection plate surrounding the lamp; and a cylindrical plug detachably and non-rotatably attached to the socket from outside;

wherein said bunched portion is inserted through said plug, and said bunched portion is fixed to the plug so that the bunched portion faces said light outlet port when the plug is attached to said socket.

4. The microfilm search device according to claim 3, wherein the reflection plate is formed into a box to surround the lamp, and a shielding plate is disposed between said light outlet port and the lamp to prevent light of the lamp from being directly radiated to said light outlet port.

5. A microfilm search device for distinguishing presence of frames from a density change in a running direction of a microfilm and searching for a desired frame from the microfilm, comprising:

a pair of blocks arranged across the microfilm in a width direction and opposed to each other with the microfilm placed therebetween;

a plurality of optical fibers whose end faces pass through and are held by the blocks are opposed to each other while the microfilm is placed between the end faces;

a light source used in guiding light to the optical fibers held by one block;

a photosensor for detecting a quantity of light incident on said the optical fibers held by the other block;

a binarizing section for binarizing an output of the photosensor; and a searching section for determining the presence of frames based on binarized signals to perform frame search;

wherein each of said blocks is formed of a metal plate exposed to a surface opposite to the microfilm and a resin integrally molded on a back side of the metal plate, a surface of said metal plate is abraded and polished, and said blocks protect the microfilm and ends of the optical fibers from inadvertent contact between the microfilm and the ends of the optical fibers.

6. The microfilm search device according to claim 5, wherein the metal plate is formed of stainless steel, and the resin formed by mixing glass fiber into polybutylene terephthalate is integrally molded on the back side of the metal plate.

7. The microfilm search device according to claim 5, wherein the metal plates of the blocks are electrically connected to each other and grounded.

8. The microfilm search device according to claim 5, wherein said metal plate is arranged across the microfilm in the width direction including a frame portion of the microfilm.

* * * * *

UNITED STATES PATENT AND TRADEMARK OFFICE
CERTIFICATE OF CORRECTION

PATENT NO.      : 6,384,896 B1
DATED           : May 7, 2002
INVENTOR(S)     : Yoshikazu Tatsuduki It is certified that error appears in the above-identified patent and that said Letters Patent is hereby corrected as shown below:

Title page,
Please delete the Assignee "Unisia Jecs Corporation" insert Assignee
-- Fuji Photo Film Co., Ltd. --

Column 9,
Line 19, delete "10A" insert -- 100A --
Line 27, delete "10A" insert -- 100A --

Column 10,
Line 46, delete "mi"

Column 12,
Line 9, delete "56" insert -- 56' --

Signed and Sealed this

Fifteenth Day of October, 2002

Attest:

Attesting Officer

JAMES E. ROGAN
*Director of the United States Patent and Trademark Office*